United States Patent [19]

Icking et al.

[11] Patent Number: 4,574,630

[45] Date of Patent: Mar. 11, 1986

[54] SAMPLER FOR A MILKING-SYSTEM VOLUMETER

[75] Inventors: Friedrich Icking, Oelde; Friedrich Stolte, Halle, both of Fed. Rep. of Germany

[73] Assignee: Westfalia Separator AG, Oelde, Fed. Rep. of Germany

[21] Appl. No.: 578,249

[22] Filed: Feb. 8, 1984

[30] Foreign Application Priority Data

Mar. 4, 1983 [DE] Fed. Rep. of Germany ....... 3307665

[51] Int. Cl.⁴ .............................................. G01N 1/10
[52] U.S. Cl. ................................. 73/202; 73/863.86; 137/625.48
[58] Field of Search ................ 73/202, 863.51, 863.61, 73/863.52, 863.82, 863.83, 863.84, 863.85, 863.86, 863.41; 137/625.48

[56] References Cited

U.S. PATENT DOCUMENTS 3,600,944 8/1971 Hutchings ......................... 73/863.61
4,423,741 1/1984 Levy ................................. 137/625.48

FOREIGN PATENT DOCUMENTS 242408 1/1965 Austria ............................. 73/863.61
3103669 8/1982 Fed. Rep. of Germany .

Primary Examiner—Bernard Nozick
Attorney, Agent, or Firm—Sprung Horn Kramer & Woods

[57] ABSTRACT

A sampler for a milking-system volumeter that can measure fractional volumes and that has both a partial-vacuumized separation chamber with an outlet that can be closed off by means of a valve piston and a measuring chamber. The valve piston associated with the outlet has a nozzle bore that opens into the separation chamber. It is followed by a nozzle channel with a runoff opening at the end facing away from the nozzle bore. The channel is closed when the valve piston is closed and opens into a line leading to the sampler's milk-collecting space when the valve piston is open. When milk flows out of the volumeter through the outlet, part of it flows into the nozzle channel through the nozzle bore and thence into the collecting space through the line. A sample is accordingly taken upon the completion of every fractional-volume measurement by the volumeter.

10 Claims, 10 Drawing Figures

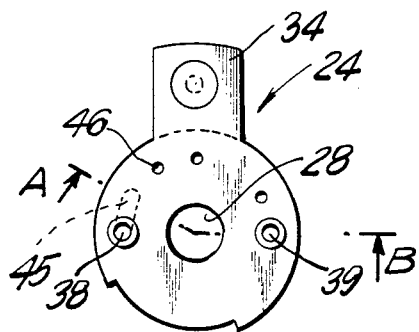
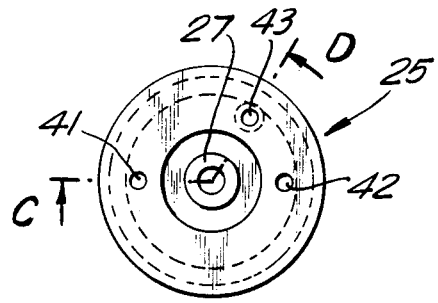
FIG. 3  FIG. 5
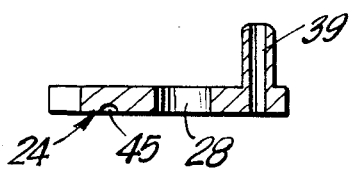
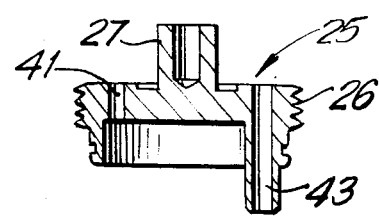
FIG. 4  FIG. 6
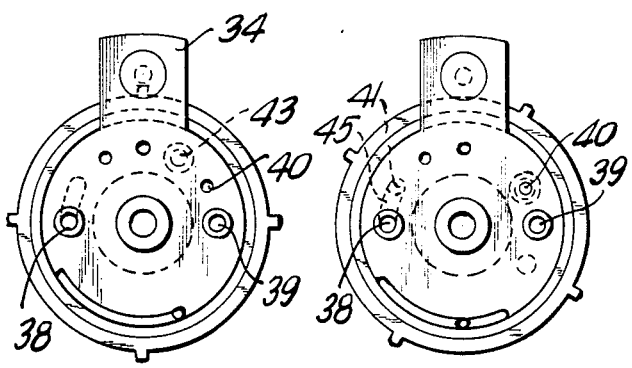
MILKING
FIG. 7
MIXING
FIG. 8
PUMPING
FIG. 9
EMPTYING
FIG. 10

SAMPLER FOR A MILKING-SYSTEM VOLUMETER

BACKGROUND OF THE INVENTION

The present invention relates to a sampler for a milking-system volumeter that can measure fractional volumes and that has both a partial-vacuumized separation chamber with an outlet that can be closed off by means of a valve piston and a measuring chamber.

A milking-system volumeter of this type is known from German OS No. 3 103 669. In this volumeter, the milk flows into a partial-vacuumized collection line when the outlet is open. One disadvantage of this volumeter is that no samples can be obtained.

SUMMARY OF THE INVENTION

The main object of the present invention is to provide a sampler for a milking-system volumeter of the aforesaid type, wherein the sampler does not cause fluctuations in the partial vacuum, the volumeter's measurement of fractional volumes is not affected, and the sample, obtained in a collecting vessel, consists of a number of fractional volumes that equal in number to the number of fractional measurements carried out in the volumeter.

This object is attained in accordance with the present invention by means of a sampler wherein the valve piston associated with the outlet has a nozzle bore that opens into the separation chamber and is followed by a nozzle channel with a runoff opening at the end facing away from the nozzle bore that is closed when the valve piston is closed and opens into a line leading to the sampler's milk-collecting space when the valve piston is open.

Since a fraction of the volume of milk flowing out of the collecting line is always removed when the outlet from the milk volumeter is open, the milk that arrives in the milk-collecting space of the sampler in accordance with the invention will always consist of fractions obtained at different intervals during milking.

The milk obtained during the first milking interval always contains much less fat than that obtained during the last interval.

The sampler in accordance with the invention ensures that a fraction corresponding to the size of the portion is obtained from each portion when a volume of milk is measured in portions. Since the size of the portion is determined by how long an emptying valve is left open, a proportionate amount of the volume of milk emptied is obtained in the form of a collective sample during emptying.

The milk in the milk-collecting space of the sampler must be mixed before it is poured into the sample bottles so that the constituents will be uniformly distributed.

Since only a small volume of milk, 20 cm³ for example, is needed for the actual testing, the excess amount in the milk-collecting space can easily be conveyed to be added to the milk already in the refrigerating tank.

In one practical embodiment of the sampler in accordance with the invention the vessel with the milk-collecting space has a stationary top on which a bottom that constitutes the lid of the vessel is mounted in such a way that it can be rotated. The top has two connections and at least one control bore and the bottom has at least two channels that can be aligned into a milking position with the connections. The bottom can be rotated in relation to the top to initiate the various operations—sampling, mixing the milk in the sampler's milk-collecting space, pumping the excess milk not needed for testing out of the collecting space, and emptying the space.

Some preferred embodiments of the invention will now be described with reference to the attached drawings, wherein

BRIEF DESCRIPTION OF THE DRAWINGS

FIG. 3 is a top view of the top of the vessel that constitutes the milk-collecting space, FIG. 4 is a section along the line A-B in FIG. 3, FIG. 5 is a top view of the bottom that constitutes the lid of the vessel, FIG. 6 is a section along the line C-D in FIG. 5, and FIGS. 7-10 are top views of various operating positions of the top and of the bottom that rotates relative to it.

DETAILED DESCRIPTION OF THE PREFERRED EMBODIMENTS

Figure 1:
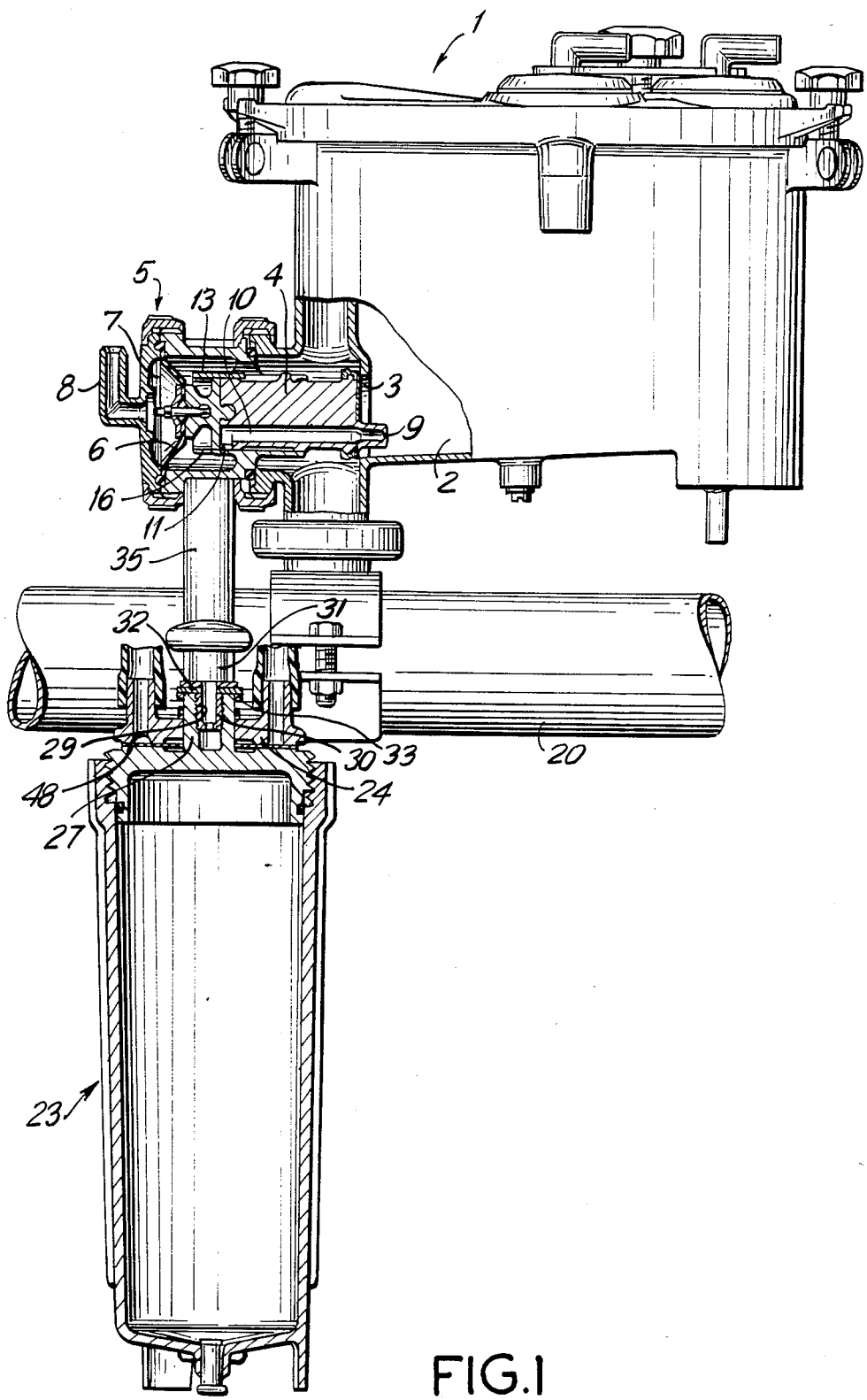
FIG. 1 is a partial vertical section of a sampler suspended on a milk volumeter with its outlet closed.

The milk volumeter 1 illustrated in FIGS. 1 and has a partial-vacuumized separation chamber 2 to which the mixture of milk and air obtained during milking is conveyed. The milk flows from separation chamber 2 into a measuring chamber in which fractional measurements are conducted. Milk volumeter 1 has an outlet 3 that can be closed off by a valve piston 4. The piston in the embodiment illustrated is fastened to a diaphragm 6 that is tensioned within a valve housing 5. Diaphragm 6 demarcates the inside of a control compartment 7 that can be subjected to air of atmospheric pressure or to a partial vacuum through a connection 8. Outlet 3 can be opened and closed with electronic controls connected to sensors positioned at intervals inside the measuring chamber.

Figure 2:
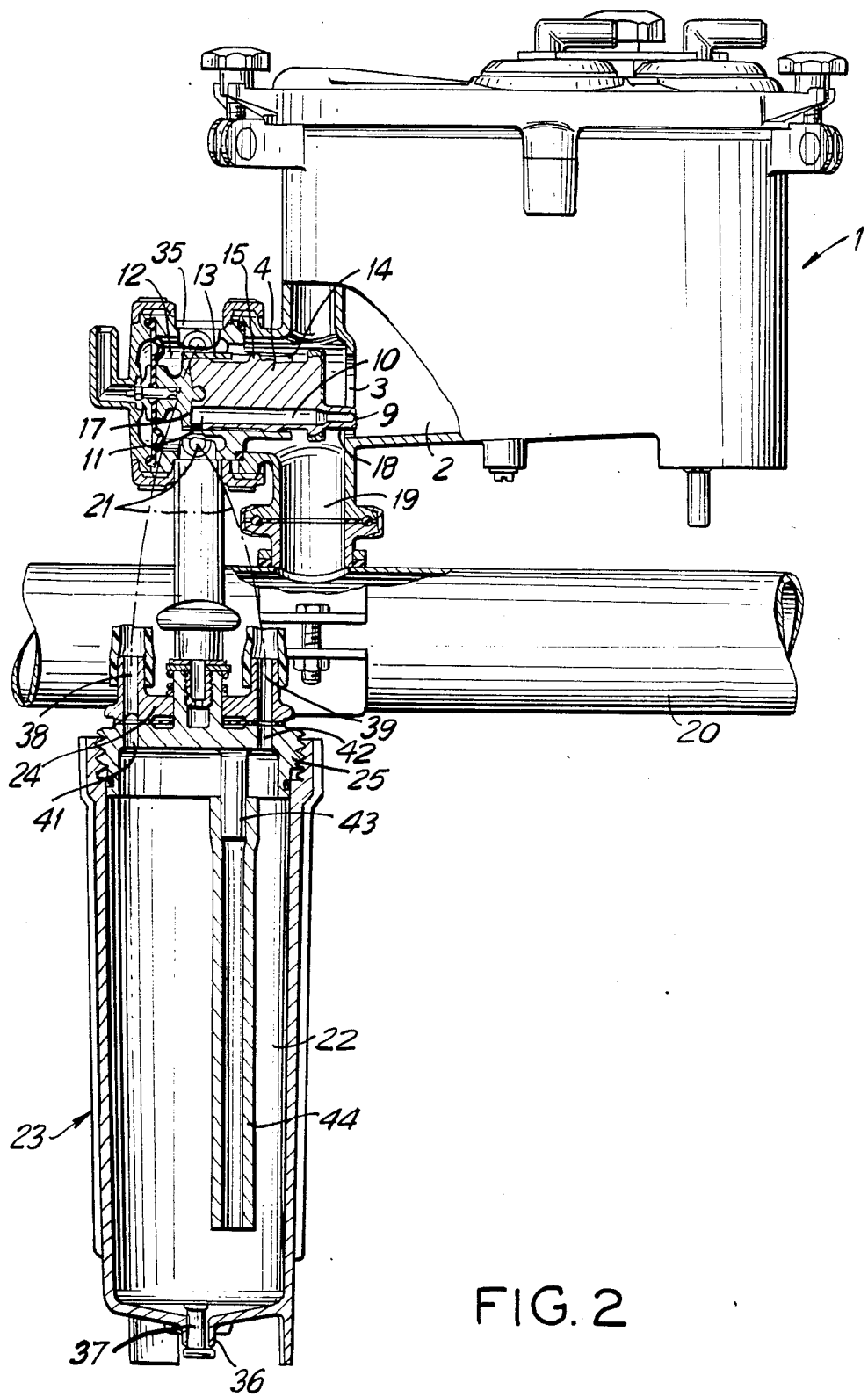
FIG. 2 is a view as in FIG. 1 but with the outlet open.

Valve piston 4 has a nozzle bore 9 that opens into separation chamber 2 and is followed by a nozzle channel 10. Channel 10 has a runoff opening 11 at the end facing away from the nozzle bore. Opening 11 is closed when valve piston 4 is closed. When piston 4 is open as illustrated in FIG. 2, opening 11 opens into a partial-vacuumized valve chamber 12 Valve piston 4 is, in the embodiment illustrated, mounted so that it can slide inside a bushing 13 that has a guide slot 14 engaged by a cam 15 on valve piston 4 to prevent the piston from rotating in relation to the bushing. The end of bushing 13 that faces away from separation chamber 2 has a slot 16. The runoff opening 11 in nozzle channel 10 is in the vicinity of slot 16 when valve piston 4 is open.

Valve piston 4 has a terminal cap 17 that blocks off the rear-face opening in nozzle channel 10. Terminal cap 17 is fastened to diaphragm 6.

The nozzle bore 9 in the embodiment illustrated is positioned in a pin 18 that projects from the face of valve piston 4 that faces separation chamber 2.

With outlet 3 open, a volume of milk flows out of milk volumeter 1 into a partial-vacuumized collecting line 20 through a line 19. A fraction of this volume flows into nozzle channel 10 through nozzle bore 9 and arrives through runoff opening 11 in another line 21 that conveys it into the milk-collecting space 22 of vessel 23.

When valve piston 4 is closed as illustrated in FIG. 1, runoff opening 11 is blocked by bushing 13 and another fractional measurement is initiated in the milk volumeter.

Vessel 23 has a stationary top 24 on which a bottom 25 that constitutes the lid of the vessel is mounted in such a way that it can be rotated. As can be seen with reference to FIGS. 3–6, threading 26 on the outside of bottom 25 screws into threading inside vessel 23. Bottom 25 rotates by means of a central pin 27 that extends through a central bore 28 in top 24. Pin 27 is hollow and has an internally threaded bushing 29 that the threaded shaft 30 of a screw 31 screws into. There is a cylindrical helical spring 33 between a washer 32 and top 24, non-positively connecting top 24 to bottom 25. There is a sliding seal, which may be a disk 48, between the mating surfaces of the top and bottom.

Top 24 has a lateral extension 34 to which a suspension bow 35, suspended in an annular groove in valve housing 5, is attached.

There is an emptying channel 36 in the floor of vessel 23. A movable valve body 37, that can be shifted into a closure position by vacuum, is positioned in emptying channel 36.

Top 24 has two connections 38 and 39 and at least one control bore 40 (FIG. 7). Bottom 25 has at least two channels 41 and 42 that can be aligned with connections 38 and 39 into the position illustrated in FIG. 2 and in which samples are taken.

Bottom 25 can be rotated in relation to top 24 to initiate various operations, which will now be described with reference to FIGS. 7–10.

The bottom 25 in the illustrated embodiment also has, in addition to channels 41 and 42, another channel in the form of a connection 43 that extends into milk-collecting space 22 and communicates with a hose 44 that extends down to the bottom of the space.

Upon termination of milking and hence of sampling, the milk in the milk-collecting space 22 of vessel 23 must be mixed. This is done by supplying atmospheric air via bore 40 through hose 44. Bottom 25 is oriented as illustrated in FIG. 8 by rotating it in relation to top 24. In this position the channel 41 in bottom 25 communicates through a channel section 45 in top 24 with the connection 38, subjected to partial vacuum, in the top. The supply of milk through connection 39 is interrupted. The control bore 40 in top 24 is in the vicinity of the connection 43 in bottom 25 that extends into milk-collecting space 22. Air flows through control bore 40 into space 22 and thoroughly mixes the milk.

Excess milk not needed for sampling is pumped out of milk-collecting space 22 first by rotating bottom 25 clockwise into the position illustrated in FIG. 9, in which a control bore 46 in top 24 is in the vicinity of the channel 41 in bottom 25. Air now flows through control bore 46 into milk-collecting space 22.

The connection 43 to bottom 26 that communicates with hose 44 is now aligned with the partial-vacuumized connection 39 in top 24 through the line 21 that leads to valve chamber 12. The pumped out milk arrives through this line and valve chamber in collecting line 20.

FIG. 10 illustrates the position of bottom 25 in relation to top 24 in which vessel 23 is emptied.

Connections 38 and 39 in top 24 are blocked off by bottom 25. Air now flows into milk-collecting space 22 through the control bore 47 in top 24 in the vicinity of the 41 in bottom 25, so that valve body 37 can shift into the opening position and the milk in milk-collecting space 22 can run off.

Thus the different operations are initiated in a sampler in accordance with the invention by very simple means.

It will be appreciated that the instant specification and claims are set forth by way of illustration and not limitation, and that various modifications and changes may be made without departing from the spirit and scope of the present invention.

What is claimed is:

1. A sampler for use with a milking-system volumeter having a partial-vacuumized separation chamber with an outlet closed off by a valve piston and a measuring chamber, the sampler comprising means forming a nozzle bore in the valve piston that opens into the separation chamber and a nozzle channel following the nozzle bore and having a runoff opening at the end facing away from the nozzle bore, means for closing the runoff opening when the valve piston is closed and for opening the runoff opening when the valve piston is opened, a milk-collecting space, a line leading from the runoff opening to the milk-collecting space to deliver milk thereto when the valve piston is open, means slidably mounting the valve piston comprising a bushing having slot at the end facing away from the separation chamber in the vicinity of the runoff opening in the nozzle channel when the valve piston is open, a valve housing having a terminal cap blocking off an opening in one face of the nozzle channel and fastened at one side of the valve piston that faces away from the nozzle bore, a diaphragm tensioned inside the valve housing and attached to the cap, and a vessel enclosing the milk-collecting space and having a lid including a stationary top on which a bottom is rotatably mounted, wherein the top has two connections and at least one control bore and the bottom at least two channels alignable into a milking position with the two connections.

2. The sampler as in claim 1, wherein the slot in the bushing empties into a partial-vacuumized valve chamber from which a milk-transport line and vacuumized line lead to the milk-collecting space.

3. The sampler as in claim 1, wherein the nozzle bore is positioned in a pin that projects from the face of the valve piston that faces the separation chamber.

4. The sampler as in claim 1, further comprising a suspension bow suspended in an annular groove in the valve housing attached to the top.

5. The sampler as in claim 1, further comprising a disk forming a sliding seal between the top and the bottom.

6. The sampler as in claim 1, wherein the bottom has a channel including a third connection that extends into the milk-collecting space and communicates with a line, that extends down to the bottom of the space.

7. The sampler as in claim 6, wherein, the bottom is rotatable to interrupt the supply of milk to the space and to align one channel in the bottom with a control bore in the top such that atmospheric air flows through into the collecting space, the other channel in the bottom remaining in communication with the vacuum line leading to the top through a section of channel in the top, whereby mixing is obtained.

8. The sampler as in claim 7, further comprising an emptying channel in the floor of vessel and a movable valve body positioned in the emptying channel and that can be shifted into a closure position by vacuum.

9. The sampler as in claim 8, wherein the bottom is rotatable into a position in relation to the top in which the connections in the top are blocked off and a channel in the bottom is aligned with a control bore in the top to permit atmospheric air to flow into the milk-collecting space, whereby the emptying is obtained.

10. The sampler as in claim 9, wherein the bottom is rotatable into a position in relation to the top in which the line leading from the bottom into the collecting space is aligned with a connection in the top and a control bore in the top is in the vicinity of a channel in the bottom thereby excess milk can be pumped out.

* * * * *